United States Patent
Li

(10) Patent No.: US 8,347,890 B2
(45) Date of Patent: *Jan. 8, 2013

(54) AUTOMATED TISSUE RETENTION SYSTEM

(75) Inventor: Kasey Kai-Chi Li, Palo Alto, CA (US)

(73) Assignee: Insono Therapeutics, Inc., East Palo Alto, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 12/617,887

(22) Filed: Nov. 13, 2009

(65) Prior Publication Data

US 2010/0294283 A1    Nov. 25, 2010

Related U.S. Application Data

(63) Continuation-in-part of application No. 12/557,760, filed on Sep. 11, 2009, now Pat. No. 8,028,705, which is a continuation of application No. 11/425,121, filed on Jun. 19, 2006, now Pat. No. 7,607,439.

(51) Int. Cl.
*A61F 5/56* (2006.01)
(52) U.S. Cl. .......... 128/848; 128/860; 602/902
(58) Field of Classification Search ........... 128/848, 128/859–861; 433/6, 31; 602/902
See application file for complete search history.

(56) References Cited

U.S. PATENT DOCUMENTS

| | | | |
|---|---|---|---|
| 4,215,984 A | 8/1980 | Reichley | |
| 4,901,737 A | 2/1990 | Toone | |
| 4,995,404 A | 2/1991 | Nemir | |
| 5,232,362 A | 8/1993 | Kanas | |
| 5,373,859 A | 12/1994 | Forney | |
| 5,464,413 A | 11/1995 | Siska, Jr. et al. | |
| 5,513,986 A | 5/1996 | Feltham et al. | |
| 5,533,470 A | 7/1996 | Rose | |
| 5,915,385 A | 6/1999 | Hakimi | |
| 5,988,170 A * | 11/1999 | Thomas | 128/848 |
| 6,422,243 B1 | 7/2002 | Daram | |

(Continued)

FOREIGN PATENT DOCUMENTS

WO    WO 2009/064914    5/2009

(Continued)

OTHER PUBLICATIONS

Colrain, I.M. et al., "A Pilot Evaluation of a Nasal Expiratory Resistance Device for the Treatment of Obstructive Sleep Apnea," *J Clin Sleep Med*, vol. 4(5): 26 pages, 2008.

(Continued)

*Primary Examiner* — Patricia Bianco
*Assistant Examiner* — Camtu Nguyen
(74) *Attorney, Agent, or Firm* — Levine Bagade Han LLP

(57) ABSTRACT

An automated tissue retention system generally comprises an oral appliance retractably coupled to a covering which is secured to an anterior portion of the tongue. Once placed within a subject's mouth, the appliance may be maintained in a closed configuration while the subject's mouth remains closed. However, as the subject sleeps and the tongue becomes hypotonic, the subject's mouth typically opens during a sleep disordered event. The appliance may be actuated by the separation between the mandible and maxilla to have greater tension and thus retract or pull anteriorly the covering adhered to the tongue. As the covering pulls the tongue anteriorly or maintains a position of the tongue, the base of the tongue may be inhibited or prevented from collapsing posteriorly against the phryngeal tissue walls and thereby allow the subject to breathe normally.

14 Claims, 16 Drawing Sheets

U.S. PATENT DOCUMENTS

| | | |
|---|---|---|
| 6,494,209 B2 | 12/2002 | Kulick |
| 6,675,804 B1 | 1/2004 | Pivovarov |
| 6,722,360 B2 | 4/2004 | Doshi |
| 6,877,513 B2 | 4/2005 | Scarberry et al. |
| 6,955,172 B2 | 10/2005 | Nelson et al. |
| 7,073,505 B2 | 7/2006 | Nelson et al. |
| 7,334,581 B2 | 2/2008 | Doshi |
| 7,607,439 B2 | 10/2009 | Li |
| 7,770,582 B2 | 8/2010 | Chen et al. |
| 7,954,494 B1 * | 6/2011 | Connor ................ 128/848 |
| 2001/0047805 A1 | 12/2001 | Scarberry et al. |
| 2002/0144685 A1 | 10/2002 | Ivanovich et al. |
| 2004/0045555 A1 | 3/2004 | Nelson et al. |
| 2004/0045556 A1 | 3/2004 | Nelson et al. |
| 2004/0049102 A1 | 3/2004 | Nelson et al. |
| 2004/0122456 A1 | 6/2004 | Saadat et al. |
| 2004/0194780 A1 | 10/2004 | Doshi |
| 2006/0000472 A1 | 1/2006 | Fenton |
| 2006/0005843 A9 | 1/2006 | Nelson et al. |
| 2006/0032497 A1 | 2/2006 | Doshi |
| 2006/0096600 A1 | 5/2006 | Witt et al. |
| 2006/0144398 A1 | 7/2006 | Doshi et al. |
| 2006/0150978 A1 | 7/2006 | Doshi |
| 2006/0150979 A1 | 7/2006 | Doshi et al. |
| 2007/0277832 A1 | 12/2007 | Doshi |
| 2007/0283962 A1 | 12/2007 | Doshi et al. |
| 2007/0289600 A1 | 12/2007 | Li |
| 2007/0295338 A1 | 12/2007 | Loomas et al. |
| 2008/0041373 A1 | 2/2008 | Doshi et al. |
| 2009/0120446 A1 | 5/2009 | Vaska et al. |
| 2009/0120447 A1 | 5/2009 | Vaska et al. |
| 2009/0123886 A1 | 5/2009 | Vaska |
| 2010/0000551 A1 | 1/2010 | Li |
| 2010/0241159 A1 | 9/2010 | Li |
| 2010/0288288 A1 | 11/2010 | Hegde et al. |
| 2010/0326448 A1 | 12/2010 | Li |
| 2010/0331877 A1 | 12/2010 | Li et al. |
| 2011/0180076 A1 | 7/2011 | Hegde et al. |

FOREIGN PATENT DOCUMENTS

| | | |
|---|---|---|
| WO | WO 2010/107461 | 9/2010 |
| WO | WO 2011/060103 | 5/2011 |

OTHER PUBLICATIONS

U.S. Appl. No. 11/425,121, filed Jun. 19, 2006 in the name of Li, Non-final Office Action mailed Feb. 21, 2008.

U.S. Appl. No. 11/425,121, filed Jun. 19, 2006 in the name of Li, Final Office Action mailed Nov. 25, 2008.

U.S. Appl. No. 11/425,121, filed Jun. 19, 2006 in the name of Li, Notice of Allowance mailed Jul. 15, 2009.

* cited by examiner

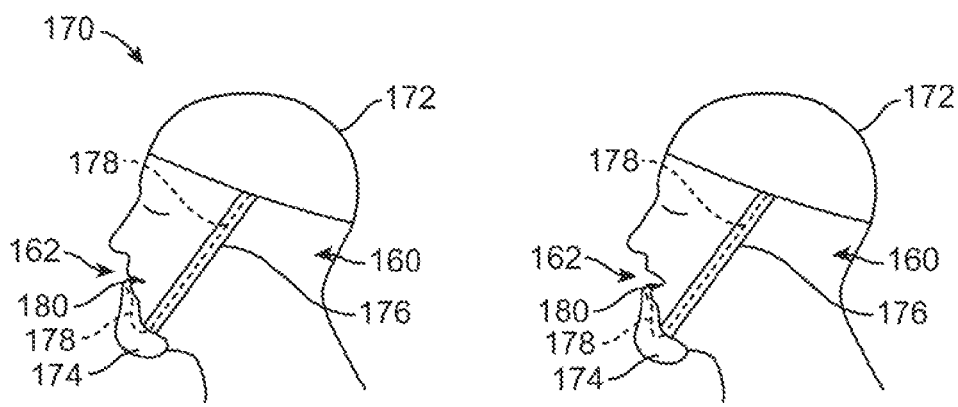
FIG. 11A
FIG. 11C
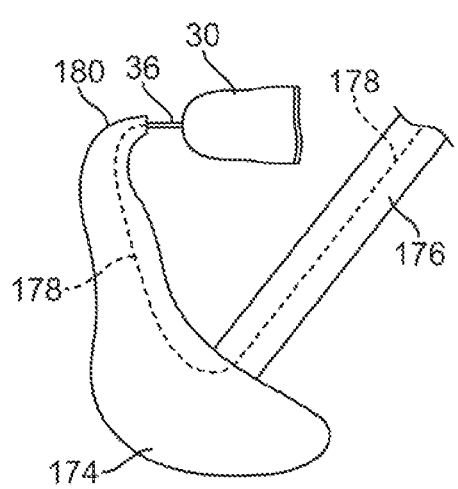
FIG. 11B
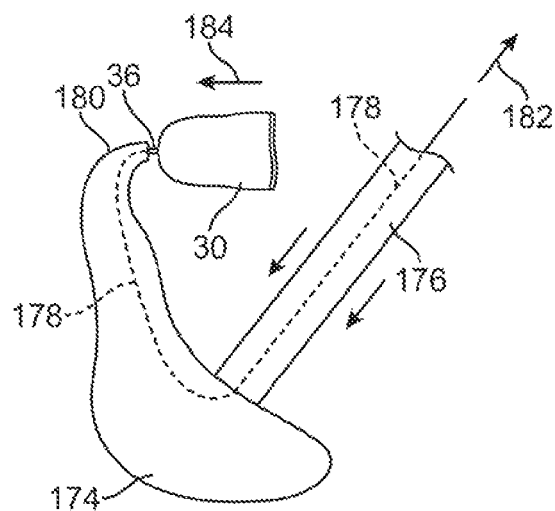
FIG. 11D

AUTOMATED TISSUE RETENTION SYSTEM

CROSS-REFERENCE TO RELATED APPLICATIONS

This application is a continuation-in-part of U.S. patent application Ser. No. 12/557,760 filed Sep. 11, 2009, which is a continuation of U.S. patent application Ser. No. 11/425,121 filed on Jun. 19, 2006 (now U.S. Pat. No. 7,607,439).

FIELD OF THE INVENTION

The present invention relates to apparatus and methods for manipulating or maintaining a position of tissue within a subject's body. More particularly, the present invention relates to apparatus and methods for protruding or maintaining a position of a subject's tongue relative to the mouth for the treatment of various disorders such as snoring, obstructive sleep apnea (OSA), chronic obstructive pulmonary disease (COPD), asthma, etc.

BACKGROUND OF THE INVENTION

The elimination of snoring and the various degrees of hypopnea and apnea have been attempted because of their various effects on the body. Such conditions typically occur due to pathological disturbances during sleep. One of the reasons of sleep disturbance is due to the tongue relaxing to varying degrees. When fully awake, the tongue has a normal tone and position within the mouth as air passes in and out of the lungs during respiration. Patency of the airway passage between the posterior wall of the pharynx and the base of the tongue is typically maintained for a normal unobstructed airway when the tongue is retained in its natural position.

However, during sleep, as the tongue becomes lax it may collapse against the posterior wall of the pharynx not only causing snoring, but also obstructing the passage of air to the lungs. When the tongue is in its relaxed and collapsed state, the base of the tongue pushes against the soft palate and also obstructs the airway passage.

Conditions such as sleep apnea not only causes drops in the blood oxygenation level, but and may also adversely affect the heart by increasing blood pressure and pulse rate. Many aspects of a person's quality of life, such as a person's physical and emotional health, are affected by obstructive sleep apnea.

A number of conventional treatments exist. For example, conventional treatments such as mask and nasal continuous positive airway pressure (CPAP) devices are typically utilized but compliance is poor and may cause discomfort in the user. Other treatments such as tongue retaining devices are typically made of soft plastic and utilize a tongue-shaped cavity to hold and maintain the tongue in a forward position. Such devices physically clamp onto the tongue using a mechanical grip or retain a portion of the tongue by utilizing a suction device. However, these methods may generally fail due to discomfort by having the tongue protruded at all times even when the patient is awake and/or breathing normally. Moreover, the tongue may not be secured by the suction device at all times.

Accordingly, there is a need for a system which maintains the patency of a person's airways during sleep and which is comfortable enough and easy to use to facilitate compliance by the user.

BRIEF SUMMARY OF THE INVENTION

Generally, an oral appliance may be placed within the subject's mouth along either the upper and/or lower dentition and allows the subject to open and close his/her mouth. The oral appliance may further comprise a covering which is coupled at a first end through or to the appliance and also at a second end to an anterior portion of the tongue (e.g., along a one-third anterior portion of the tongue). The appliance may be placed in the subject's mouth prior to sleeping and while the subject remains conscious, the appliance may be maintained in a closed configuration while the subject's mouth remains closed. However, as the subject sleeps and his/her muscles begin to relax, the tongue may transition to a hypotonic state in which muscle tone is lost. It is during this hypotonic state that a disordered breathing event, such as OSA, may occur where the base of the tongue collapses posteriorly to obstruct the subject's airways. It is also during this state when the subject's mouth will typically open and the subject will begin to breathe through the open mouth in an attempt to increase airflow.

As the subject's mouth begins to open, the oral appliance may be actuated by the separation between the jaw and maxillary to retract or pull anteriorly the covering adhered to the tongue relative to the subject's jaw. As the covering pulls the tongue anteriorly or maintains a position of the tongue, the base of the tongue may be inhibited or prevented from collapsing posteriorly against the phryngeal tissue walls and thereby allow the subject to breathe normally. A connecting member coupled to the covering may be flexible or distensible such that tongue may move comfortably within the mouth but the connecting member may retain some integrity to limit the posterior displacement of the tongue.

One example of an oral appliance may comprise an upper portion for positioning along the teeth of the maxilla and a lower portion for positioning along the teeth of the mandible. The upper portion and lower portion may be attached to one another via a hinged portion, which may be configured in any number of hinged or pivoted mechanisms such as a living hinge, etc. The oral appliance may further comprise a tongue retention covering which defines a receiving opening into which the subject's tongue may be inserted. The covering may be appropriately sized to fit upon the anterior portion of the tongue (e.g., anterior one-third portion of the tongue) and may be comprised of a distensible or flexible material such as polyethylene terephthalate (PET), silicone rubber, polyurethane, or other elastomeric materials. Additionally, the covering is sufficiently flexible such that it is able to readily conform to the tongue's changing anatomy, particularly when the tongue retains its muscular tone and when the tongue is hypotonic where muscular tone is lacking.

The covering may define along the upper and/or lower surfaces one or more ports which are either in communication with one another and/or with a common lumen defined through the connecting member which attaches the covering to either the upper or lower portions. A vacuum or suction force, e.g., 50 grams of force, may be drawn through the covering and one or more ports to adhere the covering securely onto the tongue. This vacuum or suction force may be maintained uniformly over each of the ports against either the upper (or superior) and/or lower (or inferior) portions of the tongue. Alternatively, each port may be fluidly coupled via a corresponding fluid lumen through the covering such that different ports may be actuated along the tongue surface for specified or arbitrary periods of time and/or in specified or arbitrary patterns such that different portions of the tongue are adhered to for only limited periods of time to prevent any trauma to the tissue. Such alternation of suction may be actuated via a controller incorporated into or in communication with the oral appliance.

The covering may also be coupled to one or more tensioning members (e.g., wires, cables, string, etc.) attached to a distal end of the covering and routed through the connecting member and within lumens defined through the lower portion. In this variation, a first tensioning member may pass through the lower portion to a first side of portion and exit through a corresponding opening along a surface of the portion in apposition to the upper portion, where it attaches to an attachment location on the upper portion. Similarly, a second tensioning member may pass through the lower portion to a second side of the portion and also exit through a corresponding opening for attachment at an attachment location located along the upper portion. First and second tensioning members accordingly pass through opposing sides of the lower portion and through respective openings for attachment to corresponding attachment points positioned on the upper portion on opposite ends of the appliance. Each of the openings along the lower portion and the apposed attachment points along the upper portion may be defined or positioned at various locations along the appliance provided that separation of the upper portion from the lower portion results in a tensioning of each tensioning members through the lower portion.

Each of the tensioning members may be attached to the covering through the connecting member such that during use, as upper portion is opened by the subject opening his/her mouth during a sleep disordered event, tensioning members may be pulled in the tensioning direction. The lower portion may function as a pulley as tensioning members are pulled through the lower portion to pull and retract the covering anteriorly towards the oral appliance. The number tensioning members as well as the positioning of the tensioning members relative to the oral appliance may be varied in any number of different configurations.

Turning now to the covering, it may be comprised of an outer layer and an inner layer between which one or more fluid channels may be defined in fluid communication with the one or more ports. The one or more fluid channels may be in communication with a connector fluid channel which passes through connecting member for attachment, e.g., to a pump for drawing suction within the channels. Alternatively, the covering may be comprised of a mesh covering made from any number of biocompatible materials, including but not limited to, methylmethacrylate, mersilene, silicone, polytetrafluoroethylene, polyester, polyethylene, polypropylene, etc. Fibers, strands, or ribbons of such a material may be weaved into a braided, woven, or mesh structure having a variable or uniform pitch which allows covering to conform closely to the anatomy of the tongue. Such a covering is described in detail in U.S. Pat. No. 7,607,439, which is incorporated herein by reference in its entirety.

Aside from utilizing an oral appliance anchored to the user's teeth, other variations may be employed for anchoring the device to other parts of the user's body. For instance, a chin-mounted variation which extends at least partially into the user's mouth may generally comprise a shell defining a chin receiving portion which may be contoured to mount over or rest upon the subject's chin. Generally, the shell may present a curved outline or configuration so as to prevent trauma to the user's skin and the shell may be also be optionally molded to conform to a user's particular anatomy. A separate optional strap may be attached for wrapping about the user's head to further secure the shell to the user's chin.

The chin receiving portion may be configured to secure itself at least partially about the chin such that a superior portion may extend via a flexible extension to define an open portion through which the user may position his/her mouth. A protruding member may extend within the open portion and optionally curve to extend in proximity to or at least partially within the user's mouth. A connecting member may project from the protruding member and couple to the covering while a tensioning member may extend through or from the connecting member and may pass through the tensioning member lumen defined through protruding member for attachment to the superior portion. As the subject opens and closes his/her mouth during a breathing disordered event, the flexible extension may be sufficiently flexible to allow for relative movement of the superior portion. Accordingly, the superior portion may be moved while flexing along the extension such that the tensioning member is pulled by the superior portion resulting in retraction of the connecting member through the tensioning member lumen and the subsequent anterior retraction of the covering to pull the tongue from its resting position to its retracted position. Alternative variations may utilize restraining caps or other externally anchored devices.

Another variation may utilize an assembly anchored to the lips of the user rather than the teeth or to an external anatomical feature like the chin. In use, the covering may be adhered onto the tongue of the user and the lips of the subject may be positioned within channels defined along an outer portion of respective member shaped to be received between the lips of the user similar to a lip retractor device. As the user's mouth is opened, each member may extend into its opened configuration such that a tensioning member coupling the covering and members is pulled to retract the covering anteriorly to pull the user's tongue forward or at least to limit the posterior displacement of the tongue.

Yet another variation may comprise an upper portion and lower portion for placement along the subject's dentition. Each portion may be connected to one another via a hinged portion with the covering positioned between the portions and attached pivotably at a location along the sides of the covering mid-way along its length to a first coupling member attached to the upper portion and to the second coupling member attached to the lower portion via a pivot. When the assembly is in its closed configuration, the members may be pivoted to maintain a position of the covering to maintain the position of the subject's tongue. When the subject's mouth opens, each of the portions may part from one another such that the members pivot relative to each respective portion and pull or retract the covering anteriorly or at least provides tension to limit the posterior displacement of the tongue.

In yet another variation, an assembly may generally comprise an oral appliance configured for placement along the user's upper dentition and palate. The contacting portion of the appliance may comprise a flexible portion which is integrated along the appliance. The flexible portion may be comprised of a flexible material such as polyurethane and may also comprise a first coupling member attached or otherwise secured to the flexible portion. The covering worn on the tongue of the user may also comprise a second coupling member which is positioned along the surface of covering adjacent to the appliance. In use, once the appliance and covering have been adhered or placed upon their respective positions, first and second coupling members may be attached to one another, e.g., magnetically, mechanically, etc. Once secured, the movement of the covering and the adhered tongue may be restricted to maintain the position of the tongue relative to the jaw. However, because the flexible portion is compliant, the attached covering may still move anteriorly or posteriorly by a limited distance still allowing for the user to swallow or alter a position of his/her tongue slightly for comfort.

BRIEF DESCRIPTION OF THE DRAWINGS

FIGS. 11A and 11B show side and detail views, respectively, of yet another assembly which utilizes a cap or head-mounted restraint for providing a counterforce in maintaining or moving a position of the tongue.

FIGS. 11C and 11D show side and detail views, respectively, of the assembly when the subject's mouth is opened and the tongue pulled anteriorly during a sleep disordered event.

DETAILED DESCRIPTION OF THE INVENTION

In certain breathing disorders, particularly sleep disordered breathing disorders such as snoring or obstructive sleep apnea (OSA), the subject's tongue typically collapses against the posterior wall of the pharynx obstructing the breathing airway. Treatment for such breathing disorders may generally involve maintaining a position of the tongue or protruding the tongue anteriorly relative to the subject's jaw to prevent or inhibit collapse of tissue against the phyrngeal wall.

Generally, an oral appliance may be placed within the subject's mouth along either the upper and/or lower dentition and allows the subject to open and close his/her mouth. The oral appliance may further comprise a covering which is coupled at a first end through or to the appliance and also at a second end to an anterior portion of the tongue (e.g., along a one-third anterior portion of the tongue). The appliance may be placed in the subject's mouth prior to sleeping and while the subject remains conscious, the appliance may be maintained in a closed configuration while the subject's mouth remains closed. However, as the subject sleeps and his/her muscles begin to relax, the tongue may transition to a hypotonic state in which muscle tone is lost. It is during this hypotonic state that a disordered breathing event, such as OSA, may occur where the base of the tongue collapses posteriorly to obstruct the subject's airways. It is also during this state when the subject's mouth will typically open and the subject will begin to breathe through the open mouth in an attempt to increase airflow.

As the subject's mouth begins to open, the oral appliance may be actuated by the separation between the mandible and maxilla to retract or pull anteriorly the covering adhered to the tongue relative to the subject's jaw. As the covering pulls the tongue anteriorly or maintains a position of the tongue, the base of the tongue may be inhibited or prevented from collapsing posteriorly against the phryngeal tissue walls and thereby allow the subject to breathe normally.

Figure 1:
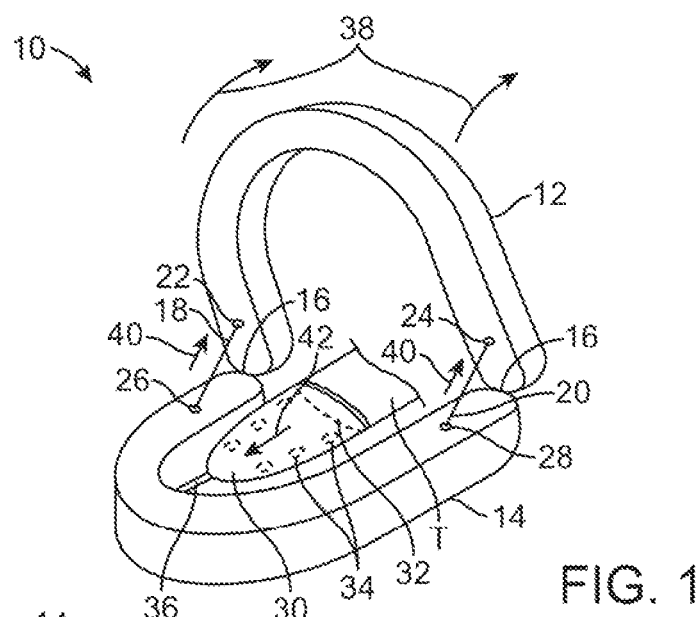
FIG. 1 shows a perspective view of one variation of the device which pulls a subject's tongue anteriorly relative to the jaw as the subject opens his/her mouth during a sleep disordered event.

Turning now to one example of an oral appliance which may be positioned within the mouth of a subject, FIG. 1 shows a perspective view of a tissue retention oral appliance 10 which comprises an upper portion 12 for positioning along the teeth of the maxilla and a lower portion 14 for positioning along the teeth of the mandible, much like a mouthguard. This particular variation illustrates a device configured to be positioned along both the upper and lower dentition; however, the oral appliance in other variations may be positioned along just the upper or lower dentition or externally of the mouth as well. Here, upper portion 12 and lower portion 14 may be attached to one another via hinged portion 16, which may be configured in any number of hinged or pivoted mechanisms such as a living hinge, etc. Alternatively, both portions 12, 14 may be completely separated from one another such that each portion may be moved independently of one another. Either or both portions 12 and 14 may comprise any number of oral appliances which may be shaped or molded (e.g., boil-and-bite thermoplastics, poly-ethylene vinyl acetate, etc.) to the specific anatomy of a particular subject or they may comprise a stock fitting for placement along the dentition.

In either case, oral appliance 10 may further comprise a tongue retention covering 30 which defines a receiving opening 32 into which the subject's tongue T may be inserted. Covering 30 may be appropriately sized to fit upon the anterior portion of the tongue T (e.g., anterior one-third portion of the tongue) and may be comprised of a distensible or flexible material such as polyethylene terephthalate (PET), silicone rubber, polyurethane, or other elastomeric materials. Additionally, covering 30 is sufficiently flexible such that the covering 30 is able to readily conform to the tongue's changing anatomy, particularly when the tongue retains its muscular tone and when the tongue T is hypotonic where muscular tone is lacking. In this variation, covering 30 may define along the upper and/or lower surfaces one or more ports 34 which are either in communication with one another and/or with a common lumen defined through the connecting member 36 which attaches the covering 30 to either the upper 12 or lower portions 14. A vacuum or suction force, e.g., 50 grams of force, may be drawn through the covering and one or more ports 34 to adhere the covering securely onto the tongue T. The one or more ports 34 may comprise a singular port or they may comprise a plurality of ports uniformly distributed over the covering. This vacuum or suction force may be maintained uniformly over each of the ports 34 against either the upper (or superior) and/or lower (or inferior) portions of the tongue. Alternatively, each port 34 may be fluidly coupled via a corresponding fluid lumen through covering 30 such that different ports 34 may be actuated along the tongue surface for specified or arbitrary periods of time and/or in specified or arbitrary patterns such that different portions of the tongue are adhered to for only limited periods of time to prevent any trauma to the tissue. Such alternation of suction may be actuated via a controller 54 incorporated into or in communication with the oral appliance.

Moreover, the controller 54 may also be used to control the vacuum or suction force through the covering 30 by maintaining the force either at a constant rate or by increasing the force in the event that the tongue T slips posteriorly from the covering 30. Accordingly, the controller 54 may be in communication with an optional pressure or force sensor incorporated into the covering 30. The controller 54 may also be optionally programmed to incorporate a delay feature with a timer function to actuate suction or differential suction after a preset period of time. For instance in one example, the timer may allow the user to fall asleep with the suction force at a comfortable first level. Once the user has fallen asleep during the preset time, the controller 54 may automatically increase the suction force or pattern to more securely adhere the covering 30 to the tongue T, particularly as the tongue T becomes hypotonic.

In yet other variations, covering 30 may also incorporate one or more openings along its outer surface for temporarily adhering the covering 30 to the user's palate by vacuum or suction if so desired to increase the securement force of the covering relative to the user's jaw.

The covering 30 may also be coupled to one or more tensioning members (e.g., wires, cables, string, etc.) attached to a distal end of the covering 30 and routed through the connecting member 36 and within lumens defined through the lower portion 14. In this variation, a first tensioning member 18 may pass through lower portion 14 to a first side of portion 14 and exit through a corresponding opening 26 along a surface of portion 14 in apposition to the upper portion 12, where it attaches to an attachment location 22 on upper portion 12. Similarly, a second tensioning member 20 may pass through lower portion 14 to a second side of portion 14 and also exit through a corresponding opening 28 for attachment at attachment location 24 located along upper portion 12. First and second tensioning members 18, 20 accordingly pass through opposing sides of lower portion 14 and through respective openings 26, 28 for attachment to corresponding attachment points 22, 24 positioned on upper portion 12 on opposite ends of the appliance 10. Each of the openings 26, 28 along lower portion 14 and the opposed attachment points 22, 24 along upper portion 12 may be defined or positioned at various locations along appliance 10, e.g., anywhere from 0 cm to 6 cm from the proximal end of appliance 10, provided that separation of upper portion 12 from lower portion 14 results in a tensioning of each tensioning members 18, 20 through lower portion 14.

Each of the tensioning members 18, 20 may be attached to covering 30 through connecting member 36 such that during use, as upper portion 12 is opened by the subject opening his/her mouth during a sleep disordered event, as indicated by the direction of movement 38, tensioning members 18, 20 may be pulled in tensioning direction 40. The lower portion 14 may function as a pulley as tensioning members 18, 20 are pulled through lower portion 14 to pull and retract covering 30 anteriorly towards the oral appliance as indicated by the direction of movement 42.

Figure 2A:
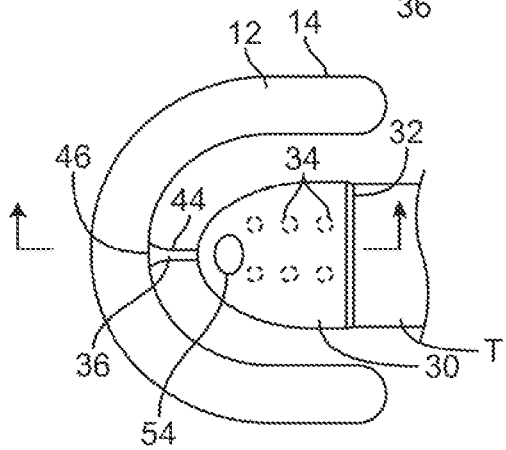
FIGS. 2A and 2B show respective top and partial cross-sectional side views of the oral appliance in a closed configuration where a covering for the tongue allows for normal positioning of the subject's tongue.
Figure 2B:
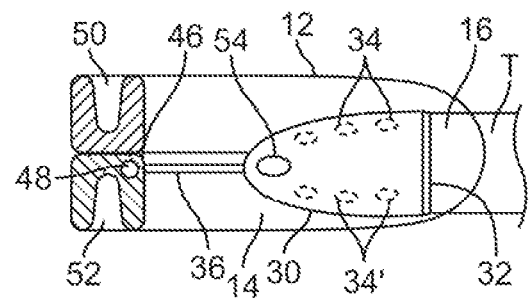

As shown in the respective top and partial cross-sectional side view of FIGS. 2A and 2B, covering 30 may be held via connecting member 36 at a first distance, e.g., 2 cm from lower portion 14, which allows the device to simply maintain a position of the tongue T relative to the jaw. The oral appliance receiving channels 50 along the upper portion 12 for receiving the teeth of the upper dentition, i.e., the teeth along the maxillary, and the receiving channels 52 along the lower portion 14 for receiving the teeth of the lower dentition, i.e., the teeth along the mandible, may also be seen. Connecting member 36 may be securely attached to a distal portion of covering 30 at attachment location 44 and through connector opening 46 defined within a posterior surface of lower portion 14 where it may pass through one or more connector lumens 48 defined at least partially through the lower portion 14.

When the oral appliance is in the closed configuration shown, e.g., where the upper 12 and lower 14 portions are placed into direct appositional contact or in proximity to one another, covering 30 is seen at a first position relative to the upper 12 and lower 14 portions. In this first position, covering 30 may be held via connector 36 at a location within the mouth in which the tongue T may comfortably rest. In the event that the user does not open his/her mouth during any breathing disordered event, covering 30 and connector 36 may simply maintain the tongue's location in this first position to prevent the posterior collapse of the tongue T or the base of the tongue in the subject's throat.

As previously mentioned and as shown, covering 30 may be adhered to the tongue T through one or more ports. In this example, the one or more ports 34 may be located along an upper (or superior) surface of the tongue T and one or more ports 34' may also be optionally located along a lower (or inferior) surface of the tongue T.

To further facilitate user comfort, connector 36 may be optionally fabricated from a flexible or distensible material (e.g., polyurethane, silicone, etc.) which allows connector 36 to elastically stretch longitudinally, e.g., a few millimeters or more, while retaining its shape and overall length. This may allow the covering 30 and the adhered tongue to retain some mobility such that lateral or posterior movement is still allowed. For instance, as the subject swallows, the tongue T may temporarily pull covering 30 posteriorly as it stretches connector 36 slightly to allow for comfortable swallowing. Once the subject is finished with the swallowing action and the tongue T relaxes again, connector 36 may pull covering 30 and the adhered tongue T anteriorly again to maintain the tongue's position and to prevent its posterior collapse. This may further allow for the maintenance of the tongue's position relative to the subject's mouth even when the mouth is closed.

Figure 3A:
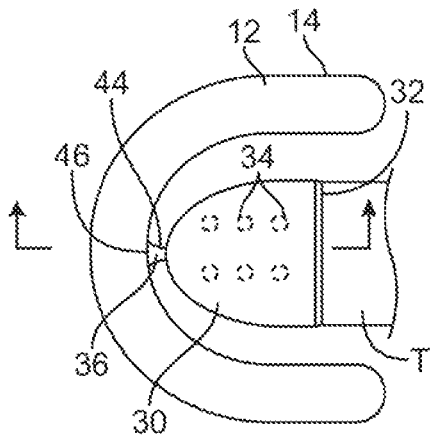
FIGS. 3A and 3B show respective top and partial cross-sectional side views of the oral appliance in an opened configuration where the covering for the tongue is retracted to pull the subject's tongue anteriorly or beyond the mouth.
Figure 3B:
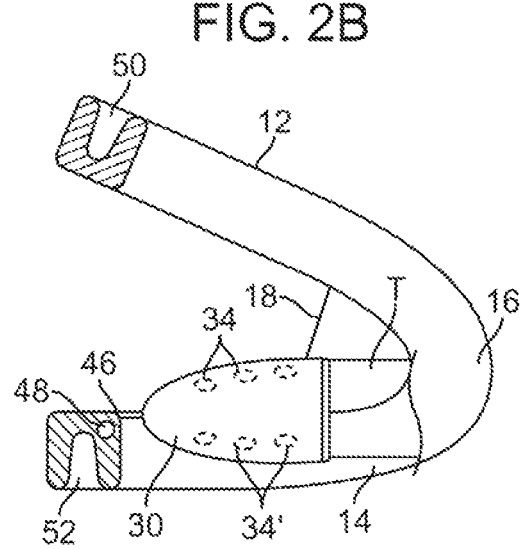

In the event that the subject undergoes a sleep disordered event, such as OSA, the subject's mouth may typically open reflexively. Once the subject's jaw opens and the lower teeth begins to move away from the upper teeth, the lower portion 14 and upper portion 12 of the oral appliance may also reconfigure into an opened configuration, as shown in the top and partial cross-sectional side view of FIGS. 3A and 3B, respectively. With connecting member 36 routed in connector lumen 48 through lower portion 14, as upper portion 12 rotates or moves away from lower portion 14, tensioning members 18 and 20 may be pulled by upper portion 12 to pull connecting member 36 and covering 30 such that covering 30 is correspondingly pulled or retracted anteriorly relative to lower portion 14 to a second retaining position thus pulling the subject's tongue T anteriorly as well to ensure the patency of the subject's airway. Lower portion 14 thus functions as a pulley to redirect the translation of connecting member 36 and effect a retracting movement of covering 30 and the adhered tongue T. With this variation, the tongue T may remain in the mouth and as the subject closes his/her mouth the tension in tensioning members 18, 20 may be released allowing connecting member 36 and covering 30 to move posteriorly back to its first position in a controlled mariner to further maintain the position of the tongue T. In this variation, the tensioning members 18, 20 may be configured and positioned along the upper 12 and lower 14 portions to retract covering 30 and the adhered tongue T over a range of distances which may be determined or set depending upon the patient's anatomy and particular OSA conditions. For example, covering 30 may be configured to move a distance of anywhere from 0 cm to 6 cm as the upper 12 and lower 14 portions reconfigure from its closed to open states.

Figure 4A:
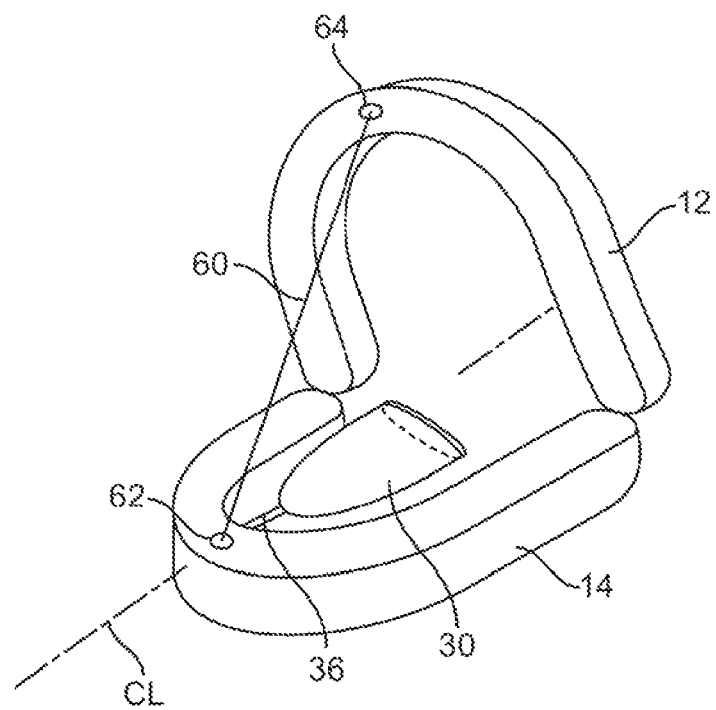
FIGS. 4A and 4B show perspective views of variations utilizing a single or double tensioning member, respectively, connected between portions of the oral appliance.
Figure 4B:
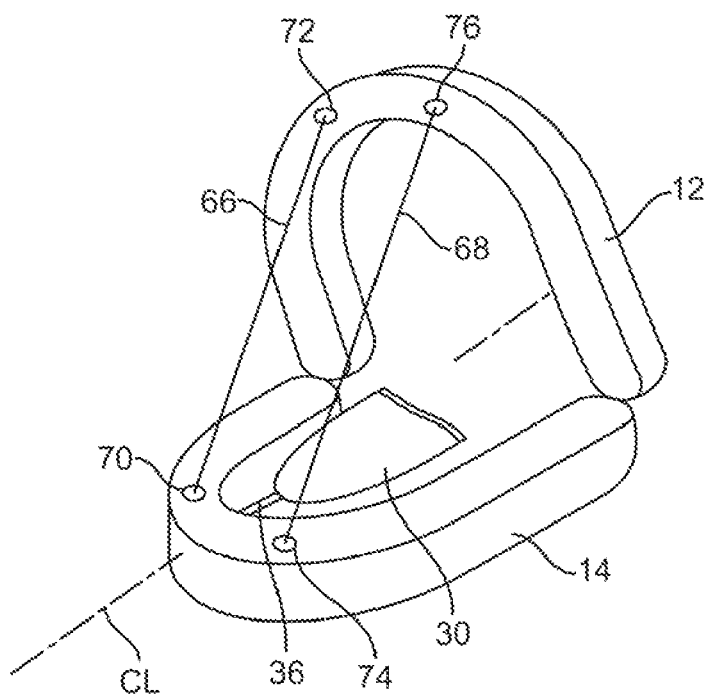

Another variation of the oral appliance is shown in the perspective view of FIG. 4A, which illustrates a single tensioning member 60 which may be attached to covering 30 via connecting member 36 through opening 62 defined along lower portion 14. The single tensioning member 60 may be positioned along a center line CL of the oral appliance and connected to upper portion 12 at attachment location 64. Yet another variation is shown in the perspective view of FIG. 4B which illustrates an oral appliance utilizing two tensioning members 66, 68 through respective openings 70, 74 along lower portion 14 for attachment to respective attachment locations 72, 76 located along upper portion 12. In this variation, tensioning members 66, 68 are symmetrically distanced from the center line CL of the oral appliance at a distance which is relatively closer to one another than in the variation disclosed above. As previously described, the tensioning members may be positioned at a range of locations along upper 12 and lower 14 portions depending upon the desired degree of retraction of the covering 30 and tongue relative to the subject's jaw.

Figure 5A:
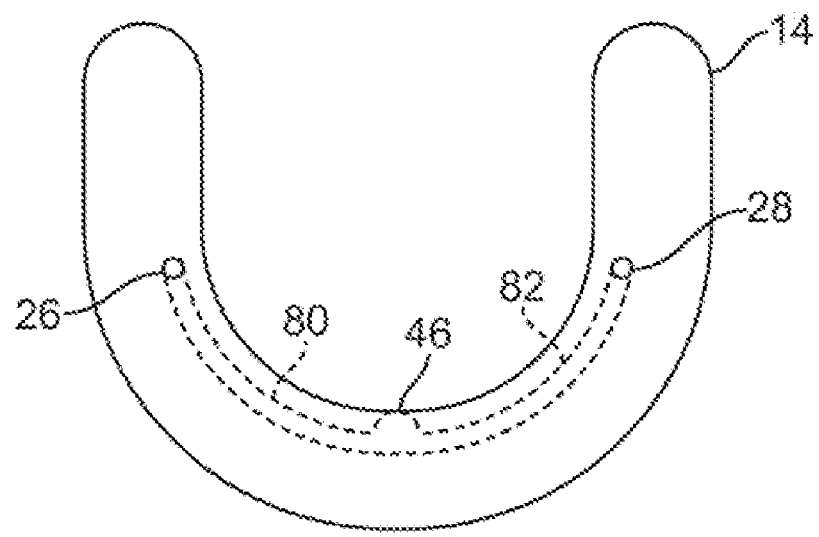
FIGS. 5A and 5B show top views of variations of the oral appliance lower portion illustrating lumen variations defined in the appliance through which the tensioning member may be positioned for coupling to the upper portion.
Figure 5B:
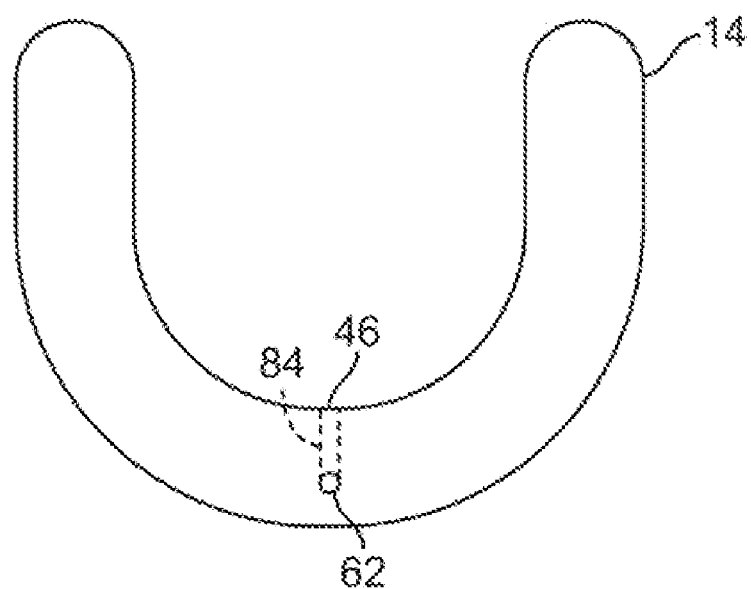

Turning to some alternative variations of the lower portion 14, FIGS. 5A and 5B show top views of lower portion 14 to illustrate an indication of how a first connector lumen 80 and second connector lumen 82 (or a single connector lumen 84) may be defined through the lower portion 14 to maintain communication between the connector opening 46 and respective openings 26, 28 (or single opening 62) through which connecting member 36 may be routed. Depending upon the number of tensioning members used, the respective connector lumens 80, 82 may be defined through the lower portion 14 while remaining in communication with connector opening 46 and/or with each lumen as well.

Figure 6A:
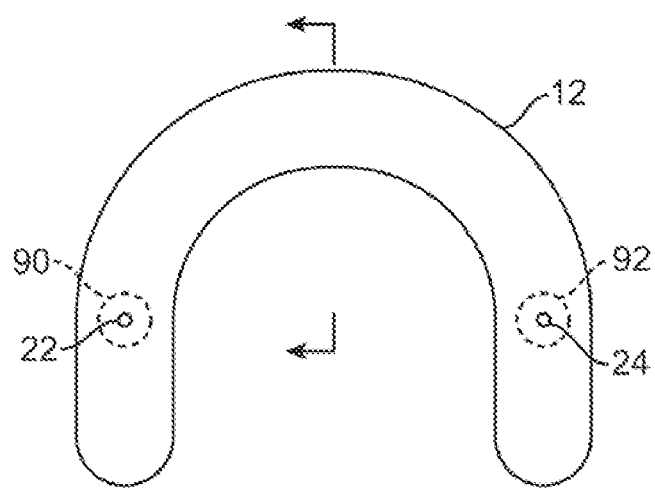
FIGS. 6A and 6B show bottom and partial cross-sectional side views, respectively, of a variation of the oral appliance upper portion showing where the one or more tensioning members may be attached.
Figure 6B:
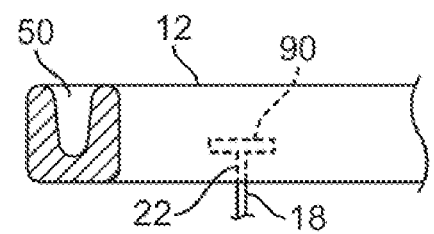
Figure 6C:
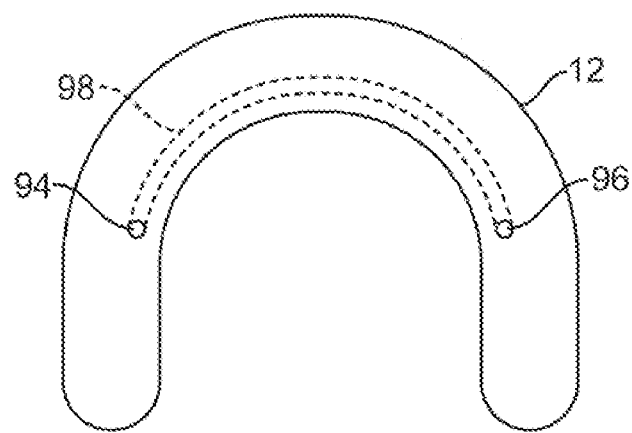
FIG. 6C shows a bottom view of another variation of the oral appliance upper portion illustrating a single lumen defined therethrough for connecting the tensioning member.

Turning now to some alternative variations on the upper portion 12, FIGS. 6A and 6B show bottom and partial cross-sectional side views of one variation of upper portion 12 illustrating an example for anchoring the tensioning members to the upper portion 12. As shown, each tensioning member may be secured to a respective first anchor 90 and second anchor 92 which may be embedded or incorporated within the upper portion 12. The anchors 90, 92 may comprise any number of materials and configurations provided that they are secured within or along the upper portion 12 and allow for secure attachment of the tensioning members through respective first 94 and second 96 openings. Alternatively, first 94 and second 96 openings may be in communication with one another through a tensioning member lumen 98 through which the tensioning members may be coupled to one another allowing them to slide through the lumen 98, as shown in the bottom view of FIG. 6C.

Figure 7A:
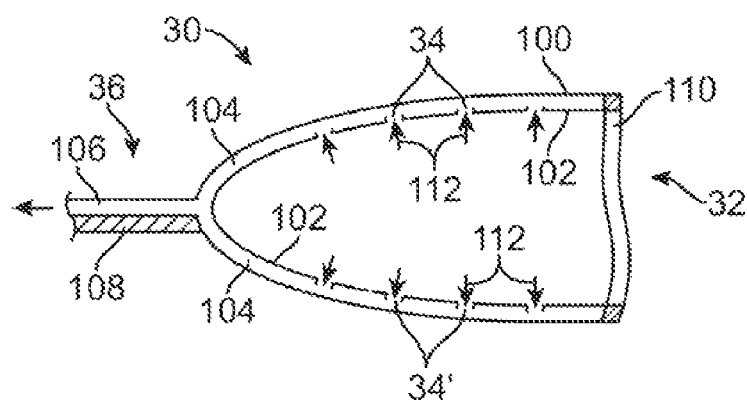
FIG. 7A shows a partial cross-sectional side view of one variation of the covering for adhering to the tongue where a fluid lumen may be incorporated with the connecting member.

Turning now to the covering, one example is illustrated in the partial cross-sectional side view of FIG. 7A. As shown, covering 30 in this variation may comprise an outer layer 100 and an inner layer 102 between which one or more fluid channels 104 may be defined in fluid communication with the one or more ports 34, 34'. The one or more fluid channels 104 may be in communication with a connector fluid channel 106 which passes through connecting member 36 for attachment, e.g., to a pump for drawing suction within the channels 104. Connecting member 36 may comprise a distensible and/or elastic member 108 to provide the elastic tension as previously mentioned. A tongue positioned through receiving opening 32 within covering 30 may be securely adhered by drawing the suction force through the one or more ports 34, 34', as indicated by force 112, to collapse covering 30 securely upon the tongue in an atraumatic manner. Covering 30 may also comprise a reinforced portion 110, e.g., integrally made from the same material as covering 30 or made from a separate flexible member and attached thereto, circumferentially positioned around opening 32 to provide, structural support for facilitating entry of the tongue into opening 32.

Figure 7B:
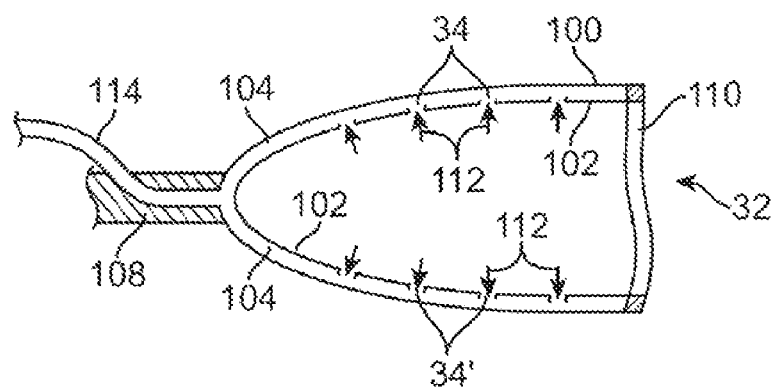
FIG. 7B shows a partial cross-sectional side view of another variation of the covering where the fluid lumen may be separated from the connecting member.

While FIG. 7A illustrates a variation of connector fluid channel 106 defined through a common connecting member 36, FIG. 7B illustrates another variation where the connector fluid channel 114 may be separated from connecting member 36 into an independent fluid channel which may be routed externally of the user's mouth and/or manipulated independently of connecting member 36.

Figure 7C:
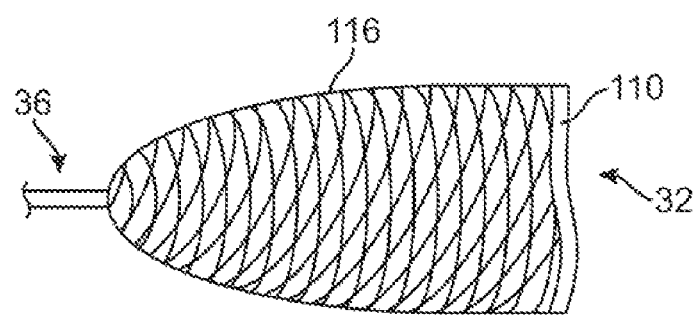
FIG. 7C shows a partial cross-sectional side view of yet another variation of the covering which may be configured from a meshed or woven material which adheres to the subject's tongue when tensioned.

FIG. 7C illustrates yet another variation for the covering which may be comprised of various materials and structures to attain the desired grip or adherence to the tongue surface. One variation, may include a mesh covering 116 placed at least partially over, upon, or around the tongue or tongue anterior. Such a covering 116 may be made from any number of biocompatible materials, including but not limited to, methylmethacrylate, mersilene, silicone, polytetrafluoroethylene, polyester, polyethylene, polypropylene, etc. Fibers, strands, or ribbons of such a material may be weaved into a braided, woven, or mesh structure having a variable or uniform pitch which allows covering 116 to conform closely to the anatomy of the tongue.

Moreover, such a braided, woven, or mesh structure may allow for the individual fibers to move and/or rotate relative to one another such that when a distal portion of covering 116 is engaged with the retaining device, the tension imparted upon the covering 116 in the axial direction may urge the braided or woven structure to restrict and conform more closely against the tongue surface. Thus, as the tongue relaxes and further collapses towards the pharyngeal tissue, the greater the retaining force imparted by covering 116 upon the tongue surface to hold and maintain its position within the patient's mouth. Additionally, covering 116 may be configured and/or adjusted by the user to cover a sufficient portion of the tongue surface so as to distribute the retaining force imparted by covering 12 evenly over the tongue to optimize comfort during use. Further details and examples of covering 116 which may be utilized with the variations herein are described in detail in U.S. Pat. No. 7,607,439, which is incorporated herein by reference in its entirety.

Figure 7D:
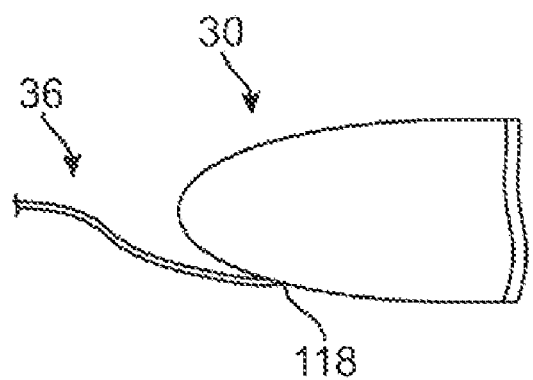
FIG. 7D shows a side view of yet another variation of the covering where the attachment point to the connecting member is located along a lower surface of the covering posteriorly of the distal tip.
Figure 7E:
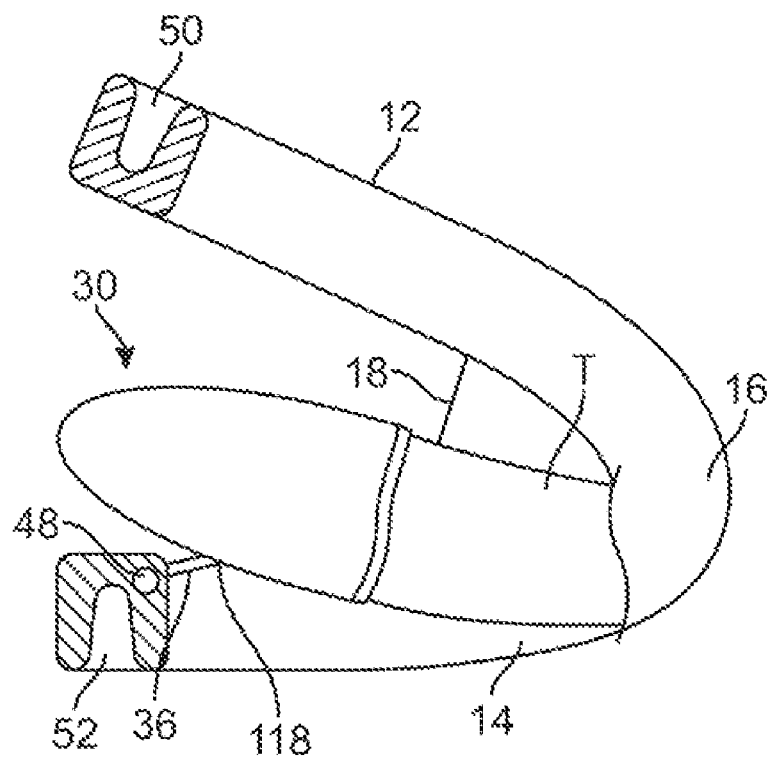
FIG. 7E shows a partial cross-sectional side view of the covering having the attachment posteriorly for protruding the tongue out of the subject's open mouth.

Another variation of the covering 30 is shown in the side view of the FIG. 7D, which illustrates connecting member 36 being attached to covering 30 at an attachment location 118 which is posterior to the distal tip. Attachment location 118 may be located anywhere from just proximal of the distal tip of covering 30 to the proximal end of covering 30. For instance, attachment location 118 may be anywhere from one-third to one-half of the length of covering 30 in some variations. Having attachment location 118 located proximally of the distal tip may allow for covering 30 and the adhered tongue T to be projected past the subject's teeth, lips, or even at least partially out of the subject's mouth depending upon the location of attachment location 118 along covering 30. Accordingly as shown in the partial cross-sectional side view of FIG. 7E, covering 30 may be pulled via attachment location 118 towards and optionally past the oral appliance or even at least partially out of the subject's opened mouth during a sleep disordered event.

Figure 7F:
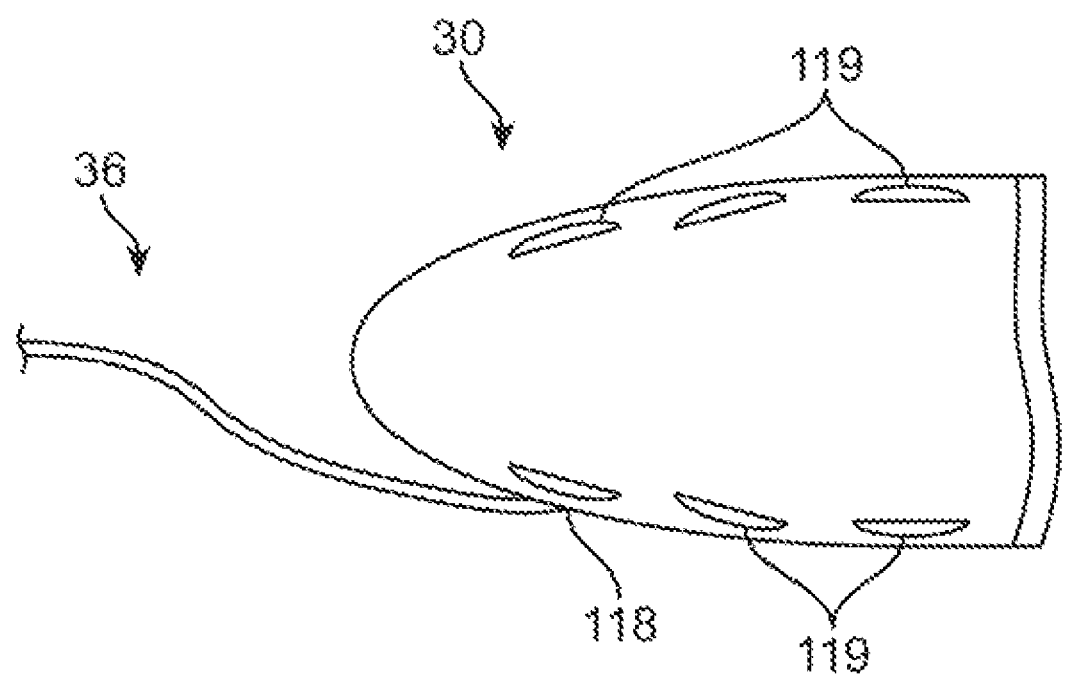
FIG. 7F shows a partial cross-sectional side view of a covering variation having one or more suction cups for adhering onto the upper and/or lower surface of the subject's tongue.

FIG. 7F shows yet another variation in a partial cross-sectional side view of a covering 30 variation having one or more suction cups 119 for adhering onto the upper and/or lower surfaces of the subject's tongue.

Figure 8A:
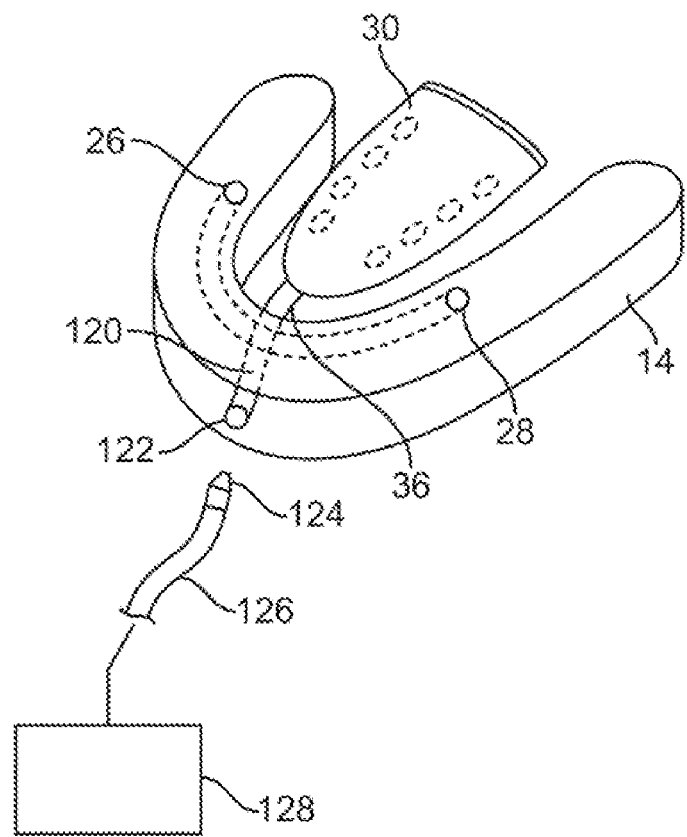
FIG. 8A shows a perspective view of a pump assembly which may be fluidly coupled to the oral appliance for providing suction to the covering.
Figure 8B:
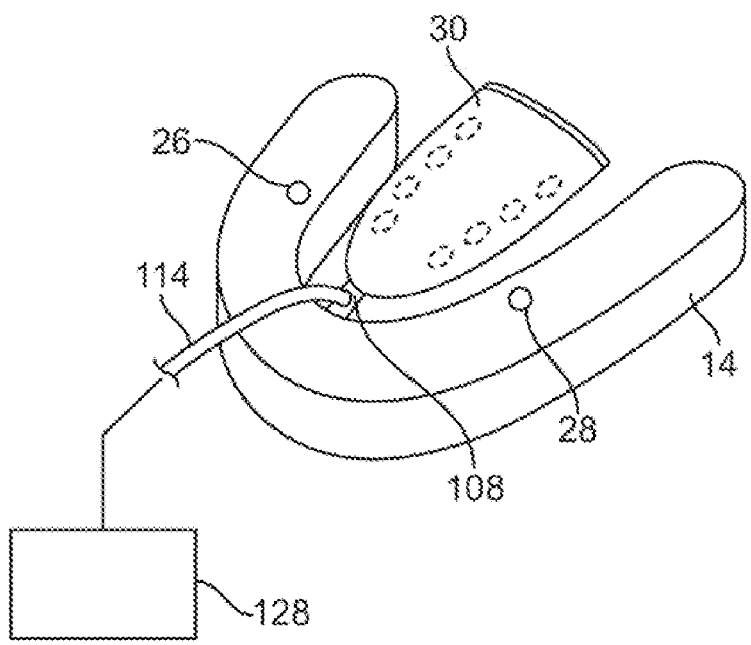
FIG. 8B shows a perspective view of another variation where the pump assembly may be coupled to a separate fluid lumen.

In drawing the vacuum or suction force for adhering the covering 30 temporarily onto the subject's tongue, FIG. 8A illustrates one variation utilizing a pump which may be located external to the subject's mouth. In this example, pump and/or controller 128 may be connected to a fluid lumen 126 having an attachment or coupling 124 thereon. The coupling 124 may be removably attached to a receiving lumen connector 122 located along either the upper 12 or lower 14 portion such that once coupling 124 is secured to lumen connector 122, pump and/or controller 128 may be in fluid communication with covering 30 through connecting member 36. A valve 120 (e.g., unidirectional valve) may be optionally incorporated within lower portion 14 in communication with lumen connector 122 such that actuation of pump and/or controller 128 to draw the vacuum or suction force through connecting member 36 and covering 30 may allow for the collapse of covering 30 onto the user's tongue but inhibits or prevents the air from flowing back through covering 30 and release of covering 30 from the tongue surface. FIG. 8B shows another variation where the separated connector fluid channel 114 may also be coupled (removably if so desired) to pump and/or controller 128.

Although the variations illustrate coupling 124 as removably attachable to lower portion 14 via lumen connector 122, fluid lumen 126 may be secured directly in a non-removable manner to lower portion 14 in a permanent connection in other variations. In use, once the oral appliance has been positioned within the patient mouth the tongue inserted into covering 30, coupling 124 may be connected to lumen connector 122 (if not already connected) and the vacuum or suction force drawn by pump and/or controller 128 to collapse and adhere the covering 30 onto the tongue. If the seal between the tongue and covering 30 is well maintained, coupling 124 may be de-coupled from lumen connector 122 leaving the oral appliance within the patient mouth with covering 30 attached to the tongue for use. After use, the seal between the covering 30 and tongue may be broken and the oral appliance removed from the user's mouth.

Alternatively, coupling 124 may be left attached to lumen connector 122 with fluid lumen 126 passing out of the subject's mouth to pump and/or controller 128 (which may be placed next to the user or which may be left to hang from the user's mouth) for continued use and/or monitoring by the pump and/or controller 128 throughout the user's sleep. In this manner, the pump may be activated automatically by the controller to maintain a seal between the covering 30 and tongue or the pump may be actuated to alter suction patterns on the tongue surface or any other features, such as a delay in suction increase, as described herein. After use is completed, the seal between covering 30 and the tongue may be broken manually or by reversing airflow through the pump and/or controller 128. Even with pump and/or controller 128 in fluid communication with covering 30, connecting member 36 may maintain its elasticity and the oral appliance may function as previously described to retract covering 30 and the tongue when the upper 12 and lower 14 portions are reconfigured.

Figure 9A:
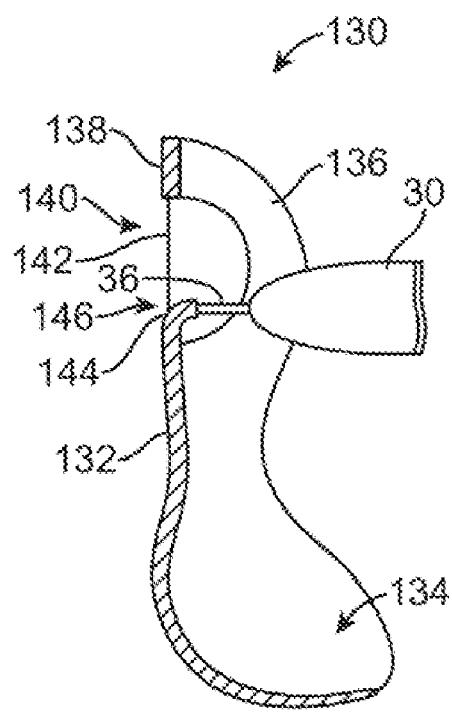
FIGS. 9A and 9B show partial cross-sectional side views of another assembly which may be positioned externally to the chin and mouth of the subject.
Figure 9B:
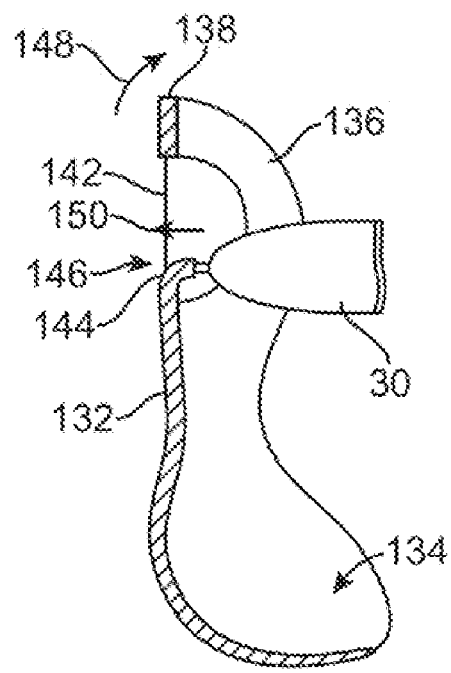

Aside from utilizing an oral appliance anchored to the user's teeth, other variations may be employed for anchoring the device to other parts of the user's body. For instance, FIGS. 9A and 9B illustrate partial cross-sectional side views of a chin-mounted variation 130 which extends at least partially into the user's mouth. This variation may generally comprise a shell 132 defining a chin receiving portion 134 which may be contoured to mount over or rest upon the subject's chin. Generally, shell 132 may present a curved outline or configuration so as to prevent trauma to the user's skin and shell 132 may be also be optionally molded to conform to a user's particular anatomy. A separate optional strap may be attached to shell 132 for wrapping about the user's head to further secure shell 132 to the user's chin.

The chin receiving portion 134 may be configured to secure itself at least partially about the chin such that a superior portion 138 may extend via a flexible extension 136 to define an open portion 140 through which the user may position his/her mouth. The flexible extension 136 portion may extend along either side of the mouth to form a superior portion 138 which extends over or rests along the user's upper lip. A protruding member 144 may extend within the open portion 140 and optionally curve to extend in proximity to or at least partially within the user's mouth. Connecting member 36 may project from protruding member 144 and couple to covering 30 while a tensioning member 142 may extend through or from connecting member 36 and may pass through tensioning member lumen 146 defined through protruding member 144 for attachment to superior portion 138.

Because superior portion 138 may become repositioned relative to shell 132 as the subject opens and closes his/her mouth during a breathing disordered event, flexible extension 136 may be sufficiently flexible to allow for relative movement of superior portion 138. Accordingly, flexible extension 136 may be a separate component from shell 132 or it may be integrally formed with shell 132. In either case, at least flexible extension 136 may be comprised of a flexible material (e.g., thermoplastics, silicone, etc.) to allow for sufficient relative movement and flexion of extension 136. As illustrated in FIG. 9B, as the user opens his/her mouth, superior portion 138 may be moved in the direction of movement 148 while flexing along extension 136 such that tensioning member 142 is pulled by superior portion 138 resulting in retraction of connecting member 36 through tensioning member lumen 146 and the subsequent anterior retraction of covering 30, indicated by the direction of movement 150, to pull the tongue from its resting position to its retracted position.

Figure 9C:
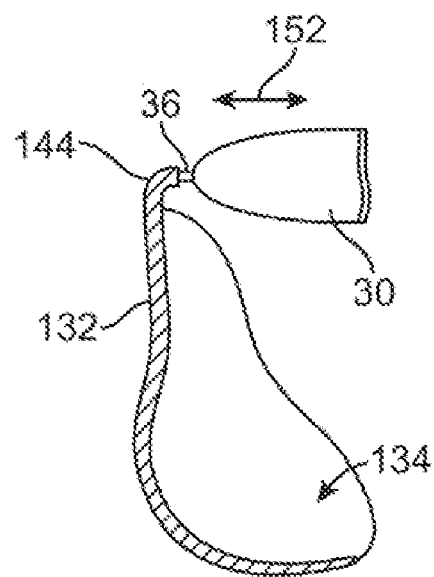
FIG. 9C shows a partial cross-sectional side view of yet another variation which may be positioned externally to the chin of the subject for maintaining a position of the tongue.

In another variation, FIG. 9C shows a partial cross-sectional side view of shell 132 and protruding member 144 with the absence of flexible extension 136 and superior portion 138. Covering 30 may be coupled to protruding member 144 via connecting member 36 to simply maintain the tongue's position relative to the jaw rather than actively retracting the tongue. Connecting member 36 may be configured to elastically permit nominal movement 152 of the covering 30 and adhered tongue such that partial movement of the tongue may be allowed during certain actions, such as swallowing as previously mentioned. In this and other chin-mounted variations, the pump and/or controller (omitted for clarity only) may also be optionally fluidly coupled by attachment directly to the covering 30 or through a fluid coupling via protruding member 144. As previously described, the pump and/or controller may be permanently or removably coupled to covering 30 or protruding member 144.

Figure 9D:
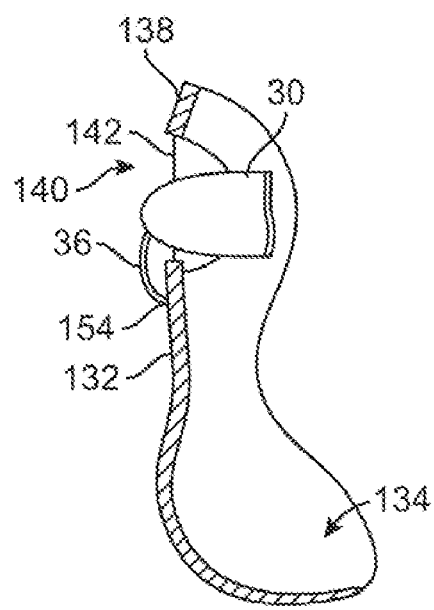
FIG. 9D shows a partial cross-sectional side view where the connecting member attached to the covering may be passed through the shell at a location external to the subject's mouth to facilitate the protrusion of the tongue past the subject's teeth and/or lips and possibly out of the mouth.
Figure 9E:
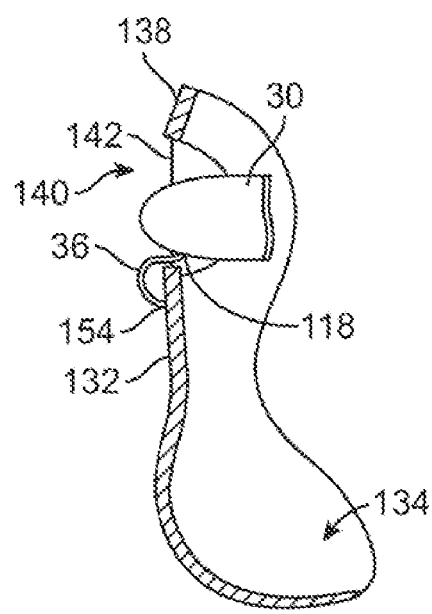
FIG. 9E shows a partial cross-sectional side view where the connecting member may be attached to the covering posteriorly of the distal tip for projecting the tongue distally.

In yet another variation, FIG. 9D shows a partial cross-sectional side view of shell 132 having an opening for the connecting member 36 located externally of the subject's mouth. When superior portion 138 is moved by the subject's mouth opening, tensioning member 142 may pull covering 30 and the adhered tongue by the connecting member 36 which may pass through shell 132 via an anchoring point or opening 154 along shell 132 located externally of the subject's mouth. By locating anchoring point or opening 154 externally of the mouth (or open portion 140), the subject's tongue may be pulled past the teeth, lips, or even at least partially out of the subject's open mouth such that covering 30 (and tongue) protrudes within or past open portion 140. FIG. 9E illustrates another variation where covering 30 may have its connecting member 36 attached at attachment location 118 located proximally of the distal tip of the covering (as described above). Connecting member 36 may pass through either an externally located anchoring point or opening 154 or through a protruding member 144, as previously shown, so long as actuation of superior portion 138 pulls covering 30 and tongue within or past the open portion 140.

Figure 10A:
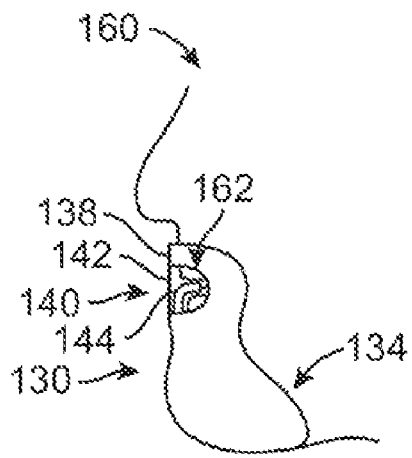
FIGS. 10A and 10B show side and front views of the device of FIG. 9A positioned on the subject with his/her mouth closed.
Figure 10C:
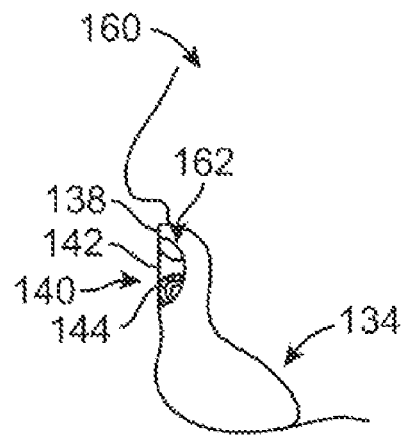
FIGS. 10C and 10D show side and front views of the device of FIG. 9B illustrating the device with the subject's mouth opened during a sleep disordered event.
Figure 10B:
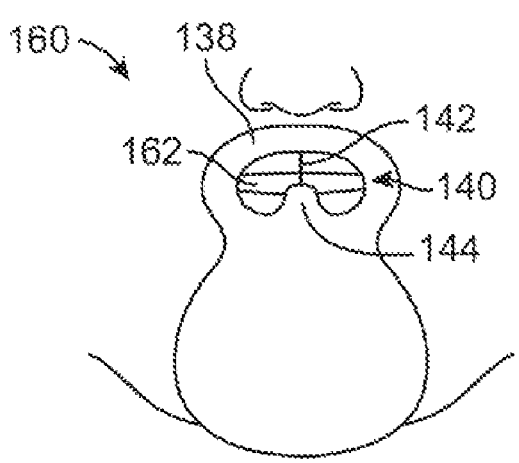
Figure 10D:
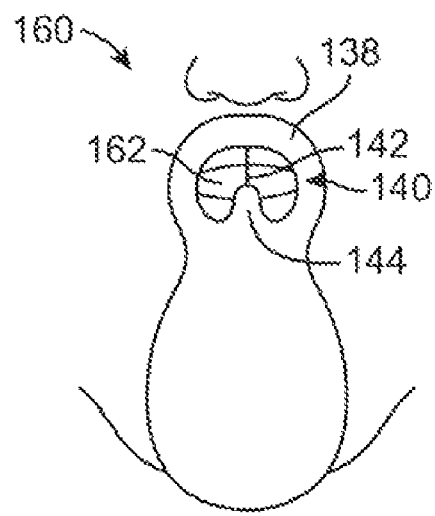

FIGS. 10A and 10B illustrate side and front views, respectively, of one example for use of the chin-mounted appliance. As shown, chin receiving portion 134 may be positioned upon the chin of subject 160 such that open portion 140 frames the subject's mouth 162. Tensioning member 142 may be seen extending between protruding member 144 and superior portion 138 over the mouth 162 while protruding member 144 may extend in proximity to or at least partially within the mouth 162. Covering 30 may be positioned over or upon the subject's tongue within his/her mouth while remaining connected via connecting member 36. While FIGS. 10A and 10B illustrate the subject's mouth 162 closed and the device in its closed configuration, FIGS. 10C and 10D show the subject's mouth 162 opened during, e.g., a sleep disordered event such as OSA. As the mouth 162 opens, superior portion 138 may be moved by the upper lip while extension 136 flexes to accommodate movement of portion 138. With portion 138 moving away from protruding member 144, the attached tensioning member 142 may be pulled through protruding member 144 to subsequently pull or retract the covering 30 adhered to the tongue from its first position to its retracted second position in which covering 30 is drawn towards protruding member 144.

Because this variation is anchored by the subject's anatomy external to the mouth, protruding member 144 may extend at a distance from the subject's mouth in alternative variations. Thus, as the subject's mouth 162 is opened and covering 30 is retracted towards member 144, covering 30 and the adhered tongue may actually be retracted to be pulled external to the mouth 162 such that the tongue protrudes at least partially past the subject's teeth and/or lips. This protrusion distance may be varied to extend any practicable distance outside the user's mouth depending upon the desired results and/or subject's anatomy.

In yet another variation where the appliance may be anchored extra-orally, FIGS. 11A and 11B show side and detail side views, respectively, of an assembly 170 which may utilize a cap restraint 172 attached to a chin restraint 174 via a connecting strap 176 located on both sides of the assembly 170. Connecting strap 176 may be fabricated from a flexible or distensible material which may elastically stretch over a distance. Chin restraint 174 may be configured similarly to the previous variation in being conformed for placement over and/or upon the subject's chin or it may be retained in position by cap restraint 172 which may be placed over and/or upon the subject's head. Cap restraint 172 may be comprised of a flexible material and sized to be situated upon at least a portion of the head. Alternatively, rather than utilizing a cap configuration, an enlarged strap may be utilized instead. In either case, a tensioning member 178 may be securely attached to cap restraint 172 to freely pass through or along either or both connecting straps 176 and through chin restraint 174 as well as protruding member 180, which may be positioned in proximity to or at least partially within the subject's mouth 162, as previously described. The distal end of tensioning member 178 may be coupled through or to connecting member 36 and/or directly to covering 30.

As the mouth of the subject opens during a sleep disordered event, such as OSA, chin restraint 174 may be moved a distance relative to cap restraint 172 as the user's jaw drops, as shown in the side view of FIG. 11C. Moreover, as the chin restraint 174, drops, connecting strap 176 may stretch elastically to accommodate the movement. Because tensioning member 178 is securely attached to cap restraint 172, which remains stationary relative to the subject 160, tensioning member 178 may be pulled in a first direction 182 relative to connecting strap 176 which moves in a second opposite direction. This counter-force may tension the member 178 through chin restraint 174 and protruding member 180 to pull or retract covering 30 in a direction of retraction 184 thereby pulling the adhered tongue anteriorly. As previously described, protruding member 180 may be positioned at least partially within the user's mouth or externally such that covering 30 and the adhered tongue may be pulled externally of the mouth.

Figure 12A:
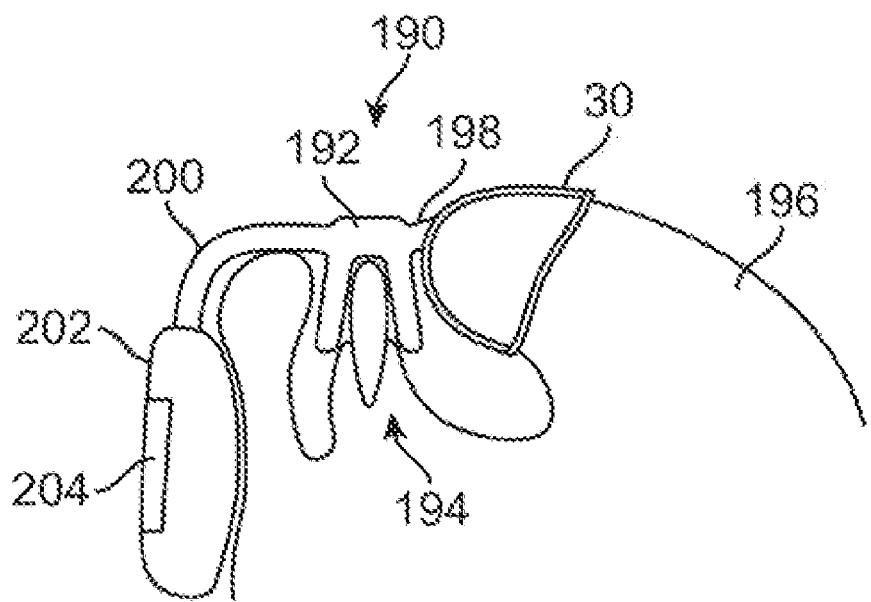
FIGS. 12A and 12B show partial cross-sectional side and detail views, respectively, of yet another variation having a pump and/or controller positioned externally of the subject's mouth.
Figure 12B:
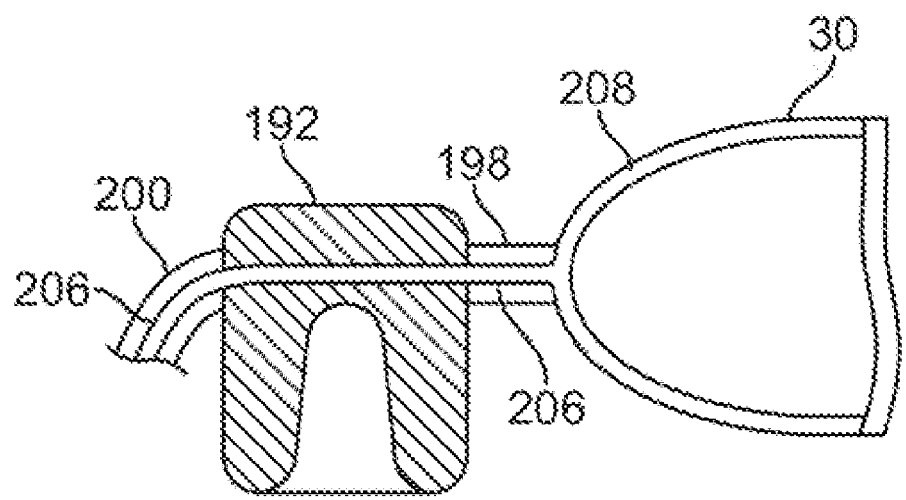

Turning now to the partial cross-sectional side and detail side views of FIGS. 12A and 12B, another intra-oral appliance is shown which utilizes an assembly 190 generally comprising a single lower portion 192 which may fit upon a portion of the user's lower dentition 194. This particular variation may comprise an assembly 190 which may be used to maintain a position of the user's tongue relative to the jaw. Covering 30, adhered to tongue 196, may be coupled to lower portion 192 via connecting member 198 and a fluid lumen 206 in fluid communication with space 208 defined in covering 30 may pass through connecting member 198 and lower portion 192. A separate pump 202 having an optional controller 204 integrated therewith may be connected to lower portion 192 via a fluid coupling 200 such that pump 202 may be situated externally of the user's mouth and used to maintain an adequate suction between covering 30 and tongue surface during use.

Figure 13A:
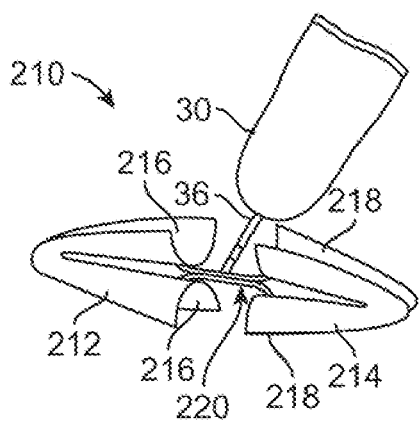
FIGS. 13A and 13B show perspective and side views, respectively, of another assembly variation where the covering may be anchored to an oral appliance shaped to be retained about the subject's lips, much like a lip retraction device.
Figure 13B:
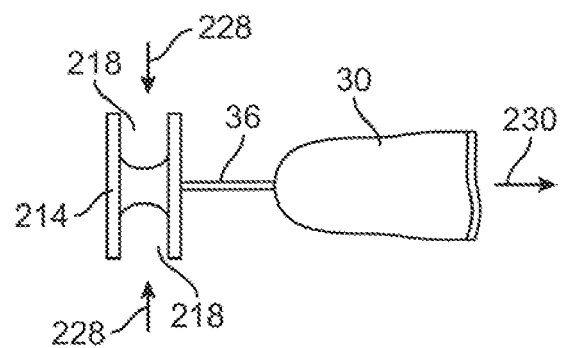
Figure 13C:
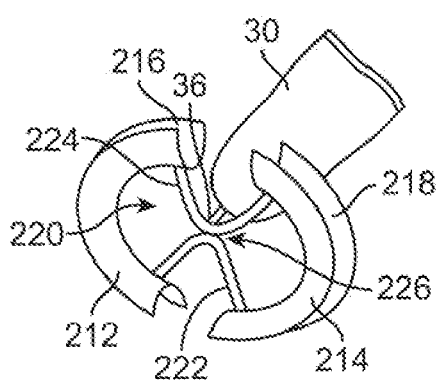
FIGS. 13C and 13D show perspective and side views, respectively, where the assembly is extended when the subject's mouth is opened to retract the covering.
Figure 13D:
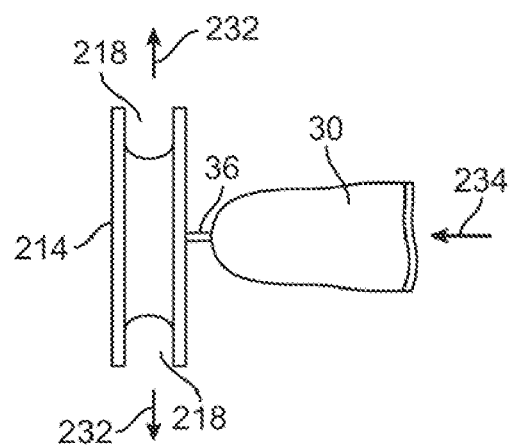

Another variation is shown in the perspective and side views, respectively, of FIGS. 13A and 13B which illustrate an assembly 210 in a collapsed configuration and FIGS. 13C and 13D which illustrate the assembly 210 in an expanded configuration. The assembly 210 may be anchored to the lips of the user rather than the teeth or to an external anatomical feature like the chin. Covering 30 may be attached by connecting member 36 to a collapsible frame assembly 220 which may comprise a first support member 222 and second support member 224 which each support a first retracting member 212 and a second retracting member 214 positioned on either side of frame assembly 220. The first and second retracting members 212, 214 may be curved in a semi-circular or semi-elliptical manner in its expanded configuration and each member 212, 214 may be positioned relative to one another in planar apposition such that the members 212, 214 together form a discontinuous elliptical shape. The collapsible frame assembly 210 may support each member 212, 214 and serve as an attachment point 226 for connecting member 36 along a central portion of frame assembly 210.

In use, covering 30 may be adhered onto the tongue of the user and the lips of the subject may be positioned within channels 216, 218 defined along an outer portion of each respective member 212, 214 and shaped to be received between the lips of the user similar to a lip retractor device. As the subject holds the assembly 210 within his/her mouth closed mouth, each member 212, 214 may be collapsed, as indicated by the direction of collapse 228, which may allow for the direction of extension 230 of covering 30, as shown in FIGS. 13A and 13B. As the user's mouth is opened, each member 212, 214 may extend into its opened configuration, as shown by the direction of expansion 232, such that a tensioning member coupling the covering 30 and members 212, 214 through frame assembly 220 is pulled to retract covering 30 anteriorly, as indicated by the direction of retraction 234, to pull the user's tongue forward, as shown in FIGS. 13C and 13D. A separate pump and/or controller (omitted only for clarity) may also be removably or integrally incorporated within frame assembly 220 or directly to covering 30.

Figure 14A:
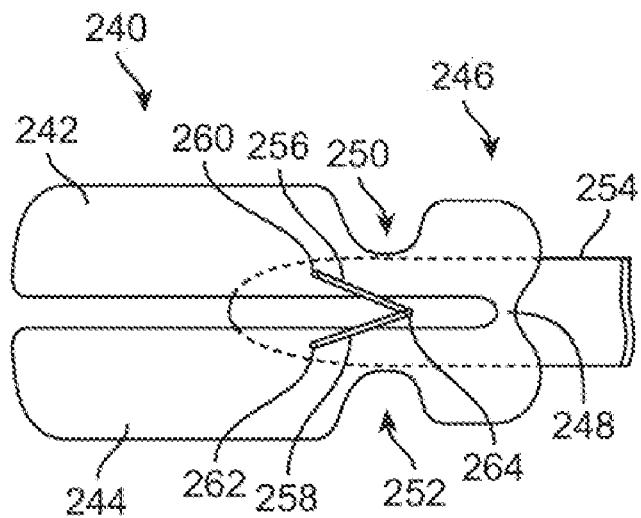
FIGS. 14A and 14B show respective side views of another variation where parting of the oral appliance urges the covering anteriorly.
Figure 14B:
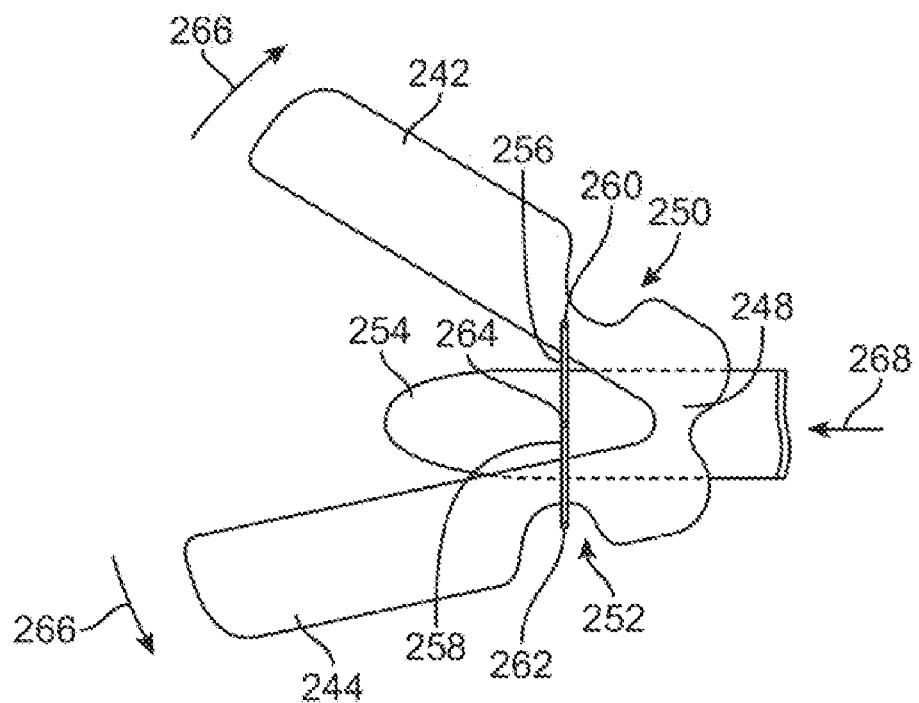

Yet another variation is shown in the side views of FIGS. 14A and 14B, which illustrate an assembly 240 having both an upper portion 242 and lower portion 244 for placement along the subject's dentition. Each portion 242, 244 may be connected to one another via a hinged portion 246 generally comprising a hinge or pivot 248 (such as a living hinge). Each portion 242, 244 may each define a respective reduced portion 250, 252 along their lengths to accommodate the appliance when moving between its closed configuration in FIG. 14A to its opened configuration in FIG. 14B. Covering 254 may be positioned between portions 242, 244 and attached pivotably at a location 264 along the sides of covering 254 mid-way along its length to a first coupling member 256 attached to upper portion 242 via pivot 260 and to second coupling member 258 attached to lower portion 244 via pivot 262. Each of the coupling members 256, 258 may comprise any number of materials and are of sufficient length such that when linearly aligned, the members 256, 258 span between the portions 242, 244 in its opened configuration. During use, when the assembly 240 is in its closed configuration, members 256, 258 may be pivoted to maintain a position of covering 30 to maintain the position of the subject's tongue. When the subject's mouth opens, each of the portions 242, 244 may part from one another, as indicated by the direction of movement 266, such that the members 256, 258 pivot relative to each respective portion 242, 244 and pull or retract covering 30 anteriorly, as indicated by the direction of retraction 268 in FIG. 14B. If the user closes his/her mouth, members 256, 258 may rotate again and move the covering 30 and adhered tongue back to its original position.

Figure 15A:
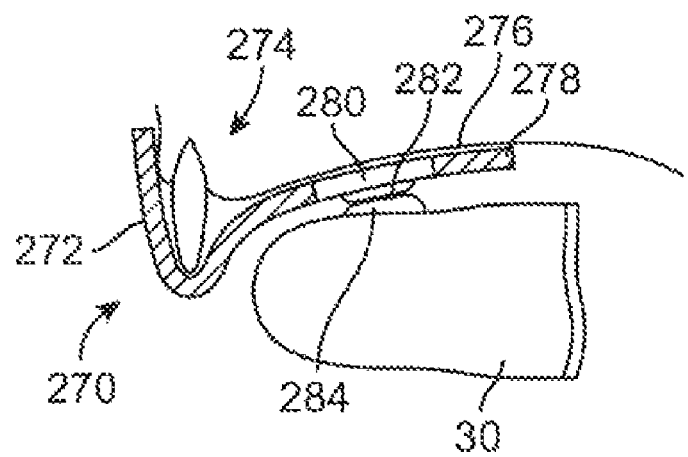
FIGS. 15A and 15B show partial cross-sectional side and bottom views, respectively, of yet another variation where the covering may be coupled to an oral appliance which allows for partial movement in multiple directions.
Figure 15B:
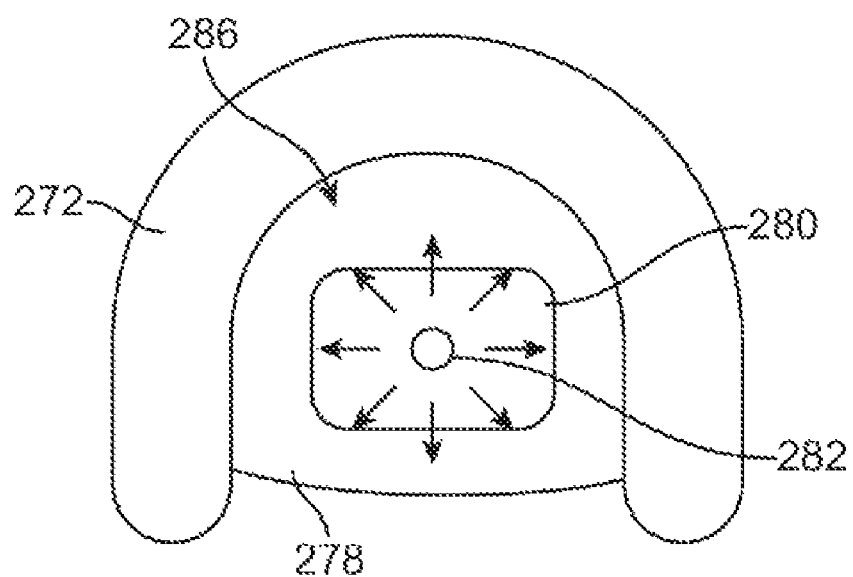

In yet another variation, FIGS. 15A and 15B show partial cross-sectional side and bottom views, respectively, of an assembly 270 which may generally comprise an oral appliance 272 configured for placement along the user's upper dentition 274 and palate 276. The contacting portion 278 of the appliance 272 which may lie along the palate 276 may comprise a flexible portion 280 which is integrated along the appliance 272. While the appliance may be molded to conform to the user's dentition, the flexible portion 280 may be comprised of a flexible material such as polyurethane and may also comprise a first coupling member 282 attached or otherwise secured to the flexible portion 280. The covering 30 worn on the tongue of the user may also comprise a second coupling member 284 which is positioned along the surface of covering 30 adjacent to the appliance 272. In use, once the appliance 272 and covering 30 have been adhered or placed upon their respective positions, first and second coupling members 282, 284 may be attached to one another, e.g., magnetically, mechanically, etc. Once secured, the movement of covering 30 and the adhered tongue may be restricted, as indicated by the direction of movement 286, to maintain the position of the tongue relative to the jaw. However, because flexible portion 280 is compliant, the attached covering 30 may still move anteriorly or posteriorly by a limited distance still allowing for the user to swallow or alter a position of his/her tongue slightly for comfort.

While illustrative examples are described above, it will be apparent to one skilled in the art that various changes and modifications may be made therein. Additionally, the devices and methods herein may be utilized to treat other breathing disorders (e.g., chronic obstructive pulmonary disease (COPD), asthma, etc.) Moreover, various apparatus or methods described above are also intended to be utilized in combination with one another, as practicable. The appended claims are intended to cover all such changes and modifications that fall within the true spirit and scope of the invention.

What is claimed is:

1. An apparatus for treating a sleep disordered event, comprising:
   an oral appliance having an upper portion and a lower portion positionable upon a dentition and sized to be positioned within a mouth of a subject, the lower portion defining at least one lumen therethrough;
   a covering which is securable in an atraumatic manner to at least a portion of a tongue,
   a connecting member coupled between the covering and the oral appliance; and at least one tensioning member coupled between the upper portion and the covering and passing through the at least one lumen and the connecting member,
   wherein opening of the mouth by the subject applies tension to the at least one tensioning member whereby the covering is retracted from a posterior position to an anterior position relative to the appliance.

2. The apparatus of claim 1 wherein the covering comprises a flexible material defining an opening for receiving the tongue.

3. The apparatus of claim 1 wherein the covering is sized for placement along an anterior portion of the tongue.

4. The apparatus of claim 1 wherein the covering defines at least one port in communication with a fluid lumen.

5. The apparatus of claim 4 further comprising a pump in fluid communication with the at least one port for drawing a vacuum or suction force therethrough.

6. The apparatus of claim 5 further comprising a controller for controlling the vacuum or suction force.

7. The apparatus of claim 5 wherein the pump is programmed to alternate the vacuum or suction force through the covering.

8. The apparatus of claim 5 further comprising a fluid lumen removably or permanently coupled to the pump.

9. The apparatus of claim 1 wherein the covering comprises a woven covering.

10. A method of treating a sleep disordered event, comprising:
    positioning an oral appliance having an upper portion and a lower portion upon a dentition within a mouth of a subject, the lower portion defining at least one lumen therethrough;
    securing a covering in an atraumatic manner to at least a portion of a tongue;
    tensioning a connecting member coupled between the covering and the oral appliance through the lower portion via the upper portion as the mouth of the subject is opened and
    retracting the covering from a posterior position to an anterior position relative to the appliance.

11. The method of claim 10 wherein securing comprises drawing a vacuum or suction force against the tongue through at least one port defined along the covering.

12. The method of claim 11 wherein drawing a vacuum or suction force comprises alternating a pattern of the force against the tongue.

13. The method of claim 10 wherein securing comprises securing the covering to an anterior portion of the tongue.

14. The method of claim 10 wherein retracting comprises urging the covering and adhered tongue towards the oral appliance.

* * * * *